(12) United States Patent
Harding et al.

(10) Patent No.: US 7,463,721 B2
(45) Date of Patent: Dec. 9, 2008

(54) SECONDARY COLLIMATOR FOR AN X-RAY SCATTERING DEVICE AND X-RAY SCATTERING DEVICE

(75) Inventors: Geoffrey Harding, Hamburg (DE); Helmut Strecker, Hamburg (DE); Dirk Kosciesza, Pinneberg (DE); Stephan Olesinski, Hamburg (DE)

(73) Assignee: GE Homeland Protection Inc., Newark, CA (US)

( * ) Notice: Subject to any disclaimer, the term of this patent is extended or adjusted under 35 U.S.C. 154(b) by 218 days.

(21) Appl. No.: 11/090,445

(22) Filed: Mar. 24, 2005

(65) Prior Publication Data

US 2005/0281383 A1    Dec. 22, 2005

(30) Foreign Application Priority Data

Mar. 24, 2004 (DE) ........................ 10 2004 014 445

(51) Int. Cl.
*G21K 1/00* (2006.01)
*G21K 1/02* (2006.01)

(52) U.S. Cl. ...................................... 378/154; 378/147
(58) Field of Classification Search .................... 378/57, 378/58, 70, 145–155
See application file for complete search history.

(56) References Cited

U.S. PATENT DOCUMENTS

| | | | |
|---|---|---|---|
| 5,099,134 A * | 3/1992 | Hase et al. | 250/505.1 |
| 5,394,453 A | 2/1995 | Harding | |
| 6,122,344 A * | 9/2000 | Beevor | 378/88 |
| 6,301,327 B1 | 10/2001 | Martens et al. | |
| 6,744,852 B2 | 6/2004 | Klotz et al. | |
| 2002/0018543 A1* | 2/2002 | Danielsson | 378/98.8 |
| 2003/0026386 A1* | 2/2003 | Tang et al. | 378/154 |
| 2004/0131158 A1 | 7/2004 | Hoheisel et al. | |

FOREIGN PATENT DOCUMENTS

| | | |
|---|---|---|
| DE | 101 36 946 A1 | 7/2001 |
| DE | 102 41 423 A1 | 9/2002 |
| EP | 0 984 302 A1 | 7/1999 |
| EP | 1 182 671 A2 | 2/2002 |

* cited by examiner

*Primary Examiner*—Irakli Kiknadze
(74) *Attorney, Agent, or Firm*—Global Patent Operation

(57) ABSTRACT

A secondary collimator for an X-ray scattering device with horizontal plates and vertical plates arranged perpendicular thereto, the vertical plates being arranged parallel to one another and being inclined by a pre-determinable scattering angle to a transmission direction of an X-ray beam, and the horizontal plates being aligned fan-shaped onto a single point, namely to the X-ray source, and the horizontal plates with the vertical plates forming a rectangular grid with the vertical plates and being combined to form a collimator unit. Moreover, the invention relates to an X-ray scattering device for baggage check with an X-ray source, with a primary collimator which only lets through a fan beam, with a secondary collimator for projecting an area of an item of luggage and with a scattering detector, the secondary collimator being arranged between the item of luggage to be examined and the scattering detector and being developed as mentioned above.

15 Claims, 3 Drawing Sheets

SECONDARY COLLIMATOR FOR AN X-RAY SCATTERING DEVICE AND X-RAY SCATTERING DEVICE

CROSS REFERENCE TO RELATED APPLICATION

This applications claims benefit of under 35 U.S.C. §119 and incorporates by reference German Patent Application No. 10 2004 014 445.1 filed Mar. 24, 2004.

1. Field of the Invention

The invention relates to a secondary collimator for an X-ray scattering device as well as an X-ray scattering device for baggage check.

2. Background

X-ray scattering devices (XRs) according to U.S. Pat. No. 5,394,453 are known. In such devices a baggage check is carried out by means of a fan beam. The fan beam is obtained through a primary slit collimator which allows merely a narrow beam of the primary radiation of an electron bremsstrahlung source to pass through. An item of luggage to be examined is struck by the fan beam. The radiation scattered from an area to be examined of the item of luggage is projected onto a detector field via a secondary collimator. The detector thus "sees", through the secondary collimator, a specific, spatially defined area of the item of luggage to be examined (tomography). However, in the case of average-sized items of luggage it is necessary to use a detector field of a large size with such a device. Due to the magnification (routinely by a factor of 2) of the item of luggage to be examined onto the detector field, detector fields approximately 1.80 m wide are already necessary for items of luggage 80 cm wide. Such a detector field can admittedly be rigidly mounted in a holding frame and thus a mechanical deformation due to the weight of the detector field and the temperature can be well monitored. The secondary collimator described in U.S. Pat. No. 5,394,453 is however self-supporting, which leads to mechanical inaccuracies and thus also involves inaccuracies in the XRs profiles measured therewith if the item of luggage to be examined exceeds a certain width.

In addition it is known to scan items of luggage by means of a conical beam. However, this requires a scanning device by means of which the item of luggage to be examined is roentgenized in a single scan. However, the throughput of items of luggage to be examined is very low in the case of such a device, as prescanning by means of a computer tomography must take place.

SUMMARY

The object of the invention is thus the provision of a secondary collimator or an X-ray scattering device which is stable and permits the recording of high-precision XRs profiles even in the case of large items of luggage to be examined.

This object is achieved by a secondary collimator according to the invention with the features of claim 1. A very compact and simultaneously rigid shape is achieved for the secondary collimator through the arrangement of horizontal and vertical plates in a rectangular grid which are combined to form a collimator unit. An unambiguous coding of an area to be examined in an item of luggage to be examined is achieved by the fan-shaped development of the horizontal plates and the parallel development of the vertical plates which are inclined by a pre-determinable scattering angle relative to the direction of transmission.

By a horizontal plate is meant within the framework of this application a plate which runs perpendicular to the XZ plane. By a vertical plate is therefore meant a plate which runs perpendicular to the YZ plane. The two terms "horizontal" and "vertical" respectively are arbitrarily chosen, as the XZ plane does not necessarily run in the vertical and the YZ plane necessarily in the horizontal. This also depends among other things on the fitting of the X-ray scattering device.

An advantageous development of the invention provides that the plates are made from an X-ray absorbing material, in particular steel, and less than 1 mm, in particular approx. 100 µm, thick. It is thereby ensured that merely the scattering radiation from the area to be examined of the item of luggage strikes the detector for which the respective detector element is coded.

A further advantageous development of the invention provides that, at the end remote from the X-ray source, the rectangular grid is 1-10 mm wide in the direction of the vertical plates and 0.5-2.5 mm high per grid element in the direction of the horizontal plates. It is thereby achieved that each grid element of the secondary collimator corresponds at its detector-side end to an element of the detector field in terms of size and there is thus an unambiguous allocation of the scattering radiation passing, through the respective element.

A further advantageous development of the invention provides that the collimator unit is 350 mm wide overall at the end remote from the X-ray source in the direction of the vertical plates and at the same time, at its end near the X-ray source in the direction of the vertical plates, 228 mm wide overall and 250 mm high overall towards the X-ray source and has an aperture of 12°. With such a collimator unit, a module is created which can be used precisely five times with a normal fan beam with an aperture of 60°. Thus a complete coverage of the entire aperture of the fan beam or else only a part-area is possible, depending on the application case.

A further advantageous development of the invention provides that the collimator unit is arranged in a vertical steel container. It is thereby possible, if two or more collimator units are arranged next to each other as a module, to achieve a very precise alignment between them.

A further advantageous development of the invention provides that five collimator units are joined together which have a total aperture of 60°. The total aperture range of the fan beam of the X-ray source is thereby covered and a swivelling of the collimator in connection with the detector need not be undertaken in order to be able to examine the item of luggage to be examined in one pass.

A further advantageous development of the invention provides that a number of metal sheets which have folded surfaces is arranged on a robust, rigid base plate, each of the adjoining surfaces standing perpendicular on one another and the first metal sheet being firmly connected to the base plate and the second metal sheet being firmly connected to the first metal sheet and the respective next metal sheet being firmly connected to its predecessor. A very stable and rigid scattering collimator is thereby obtained, which leads in the detector to a high-precision XRs profile of the area to be examined in the item of luggage to be examined.

A further advantageous development of the invention provides that a total of 18 metal sheets are arranged on the base plate. By using a total of 18 metal sheets, a collimator unit is created which extends over the entire length of the detector field.

A further advantageous development of the invention provides that, at the end opposite the base plate, the metal sheet is firmly connected to a robust, rigid cover plate. Through the use of a cover plate, an even higher rigidity of the collimator unit is achieved.

In addition, the object is achieved by an X-ray device according to the invention with the features of claim 10.

An advantageous development of the X-ray scattering device according to the invention provides that a transmission detector is arranged additionally in straight extension from the X-ray source over the area to be examined of the item of luggage. It is thereby possible that shielded areas in the item of luggage to be examined are recognized, a correction of the attenuation effects in respect of scatter data can take place and a pre-scan X-ray image of the item of luggage to be examined is obtained.

A further advantageous development of the X-ray scattering device provides that the secondary collimator is aligned in vertical direction parallel to the fan beam and aligned in horizontal direction to the area to be examined of the item of luggage. It is thereby possible to examine the item of luggage to be examined without a swivelling or axial movement of the secondary collimator and of the detector field if the item of luggage to be examined is moved between the primary collimator and the secondary collimator over a conveyor belt.

BRIEF DESCRIPTION OF THE DRAWINGS

Advantageous versions of the invention are further described with the help of the drawings. These show in detail.

DETAILED DESCRIPTION

Figure 1:
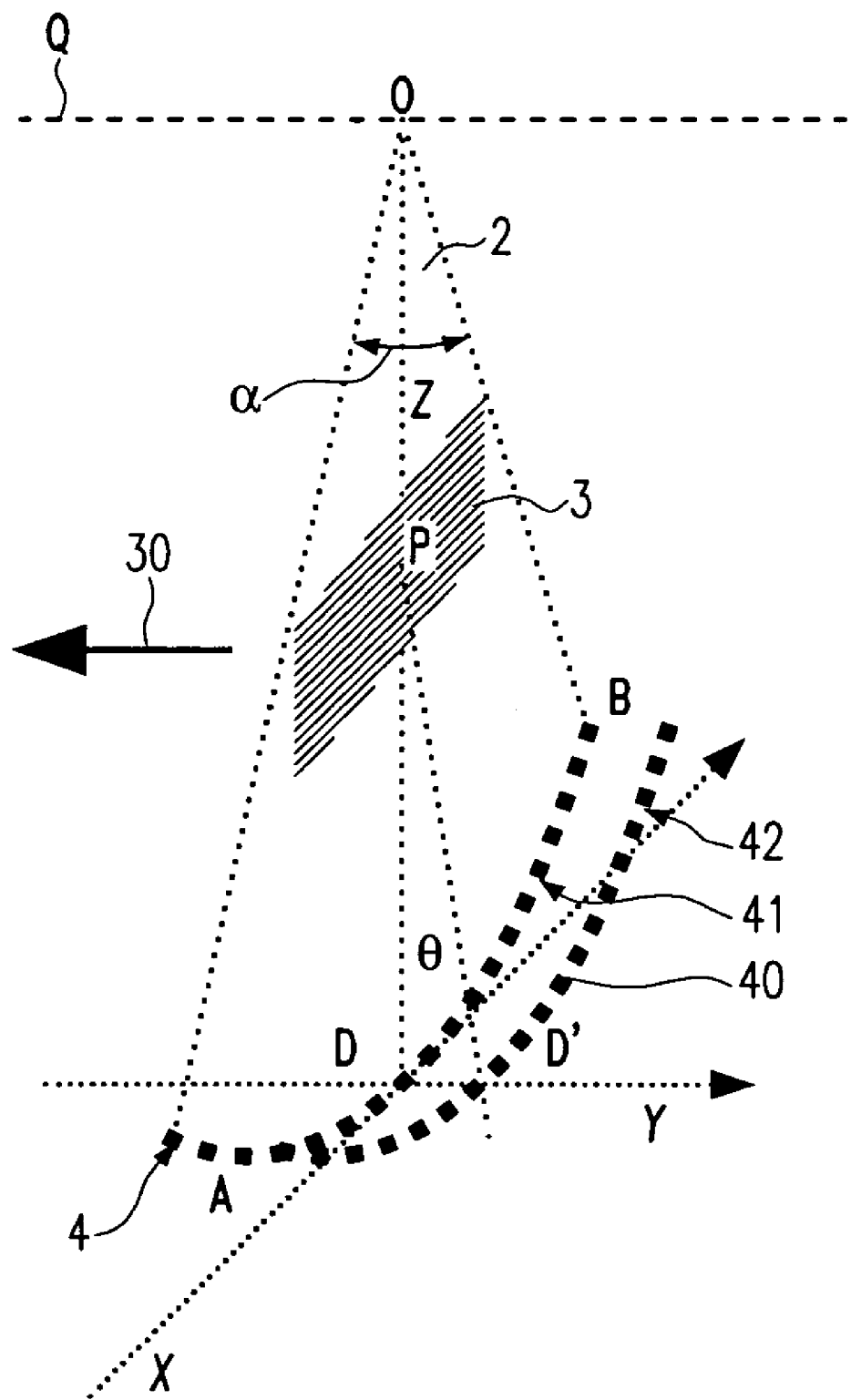
FIG. 1 A schematic perspective view of an X-ray scattering device according to the invention without primary collimator and secondary collimator, FIG. 2 a cut from a section through the X-ray scattering device according to FIG. 1 in the YZ plane with secondary collimator and part of the detector field, FIG. 3 a cut from a section through the X-ray device according to FIG. 1 along the XZ plane with partially displayed scattering collimator and FIG. 4 a schematic representation of a partially assembled secondary collimator.

A perspective view of a schematically represented X-ray scattering device is reproduced in FIG. 1, from which, however, in particular a primary collimator and a secondary collimator 1 have been omitted for the sake of clarity.

A fan beam 2 is generated by an X-ray source O by means of a primary collimator (not shown). The slit-shaped primary collimator is made of a material which strongly absorbs X-rays, for example copper or a lead compound. An electron bremsstrahlung source in the high-capacity range (for example 15 kW) and of medium voltage (for example 180 kV) is used as X-ray source O. A slit collimator which lets only a thin fan beam 2 through onto the item of luggage 3 to be examined is used as primary collimator. Both the X-ray source O and the primary collimator are known in principle and not essential to the invention, and so their design is not discussed in more detail.

All the main components of the device are rotation symmetrical relative to the given axis Q. The fan beam 2 allowed through by the primary collimator has an aperture α of 60° and is approximately 1 mm thick in Y direction.

Scattering point P represents all the scattering points of an item of luggage 3 to be examined within the fan beam 2. The Z axis is defined by the X-ray source O and the scattering point P. The X-radiation transmitted along the Z axis strikes a detector 4 at transmission point D. This transmission point D defines the origin of the Cartesian coordinates system X, Y, Z. The X axis is defined such that it runs parallel to the plane in which the aperture a of the fan beam 2 extends. On the Y axis running perpendicular to the X axis and Z axis, a scattering beam strikes a further detector element 40 of the detector 4. The coding of the scattering point P in the item of luggage 3 to the given scattering beam point D' takes place via the geometry of the secondary collimator 1, which is described below in connection with FIGS. 2 and 3.

The scattering angle Θ between the transmission point D and scattering beam point D' runs in the YZ plane.

The detector 4 used is a room temperature semiconductor, such as for example CdZnTe. The detector 4 is developed as a two-dimensionally segmented detector field. For reasons of clarity, only two rows of detector elements 40 are represented. A first row of detectors 41 runs in the XZ plane through the transmission point D. A second row of detectors 42 of detector elements 40 runs through the scattering beam point D'. The first row of detectors 41 extends in X direction from the starting point A to the finishing point B of the detector 4. These two points are defined by the aperture α of the fan beam 2. The surface of the scattering detector 4 is segmented in steps of approximately 1.5 mm in Y direction and approximately 2 mm in X direction. Each individual detector element 40 is connected to a known analysis device. Such devices are known and not essential to the invention and so their more precise design is not discussed in the following.

The overall detector field is approximately 1755 mm high in X direction and approximately 27 mm wide in X direction. Thus the scattering detector 4 has 175 segments in X direction and 18 in Y direction. This gives a total of 3150 detector elements 40. With such a scattering detector 4, an item of luggage 3 1000 mm long in Y direction can be scanned in 5 seconds with a data recording time of 5 ms per scanned millimeter if the item of luggage 3 is moved along movement direction 30 on a conveyor belt (not shown).

It is equally possible to arrange the whole scattering detector 4 with its division or else only a part of same on the other side of the fan beam plane so that a doubling of the detected scattering signal is obtained.

The signal in a transmission detector 43 which is located at the transmission point D is used to check for a shielding in the area around the scattering point P in the item of luggage 3. The transmission signal obtained can also be used to correct the attenuation effects of the scattering data and to obtain a pre-scan X-ray image of the item of luggage 3.

Figure 3:
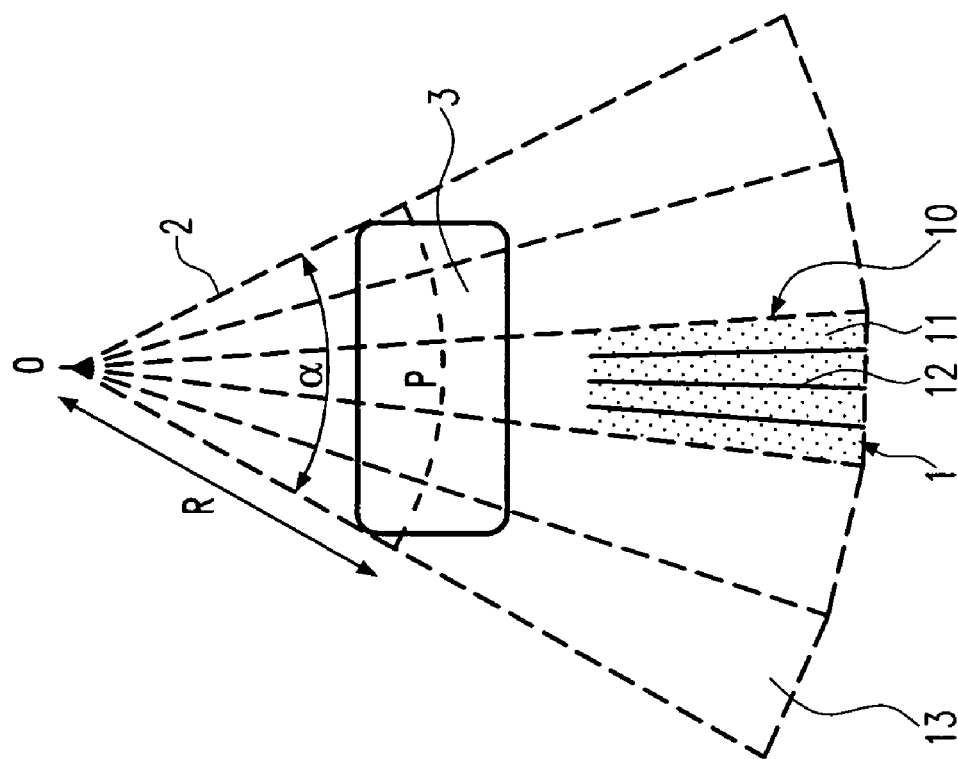
Figure 2:
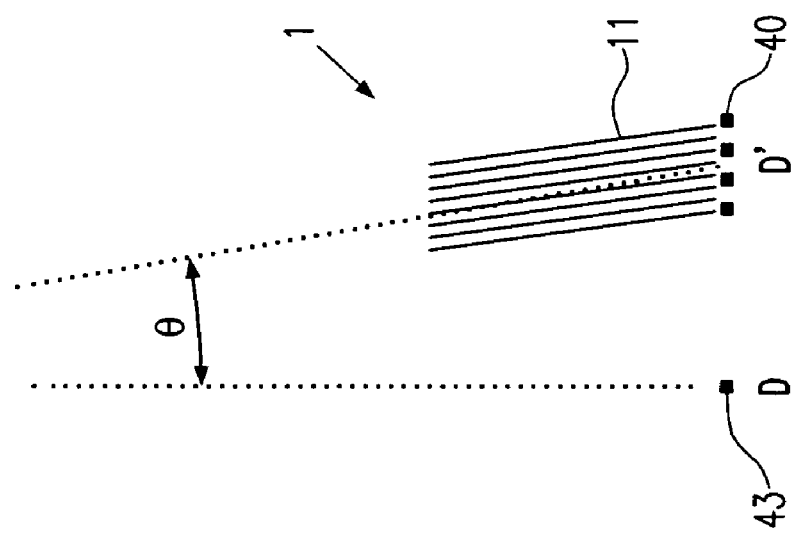
Figure 4:
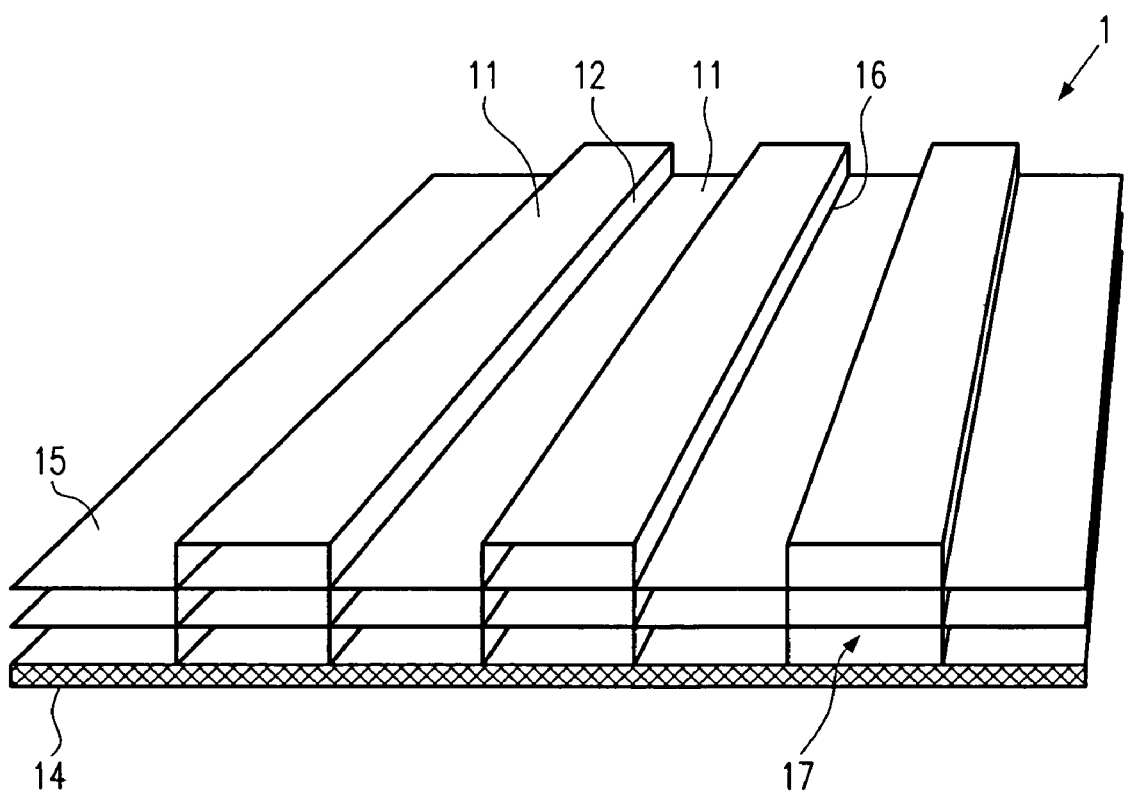

In FIGS. 2, 3 and 4 the secondary collimator 1 is shown which is described in detail below. It codes the angle at which the scattering point P is arranged relative to aperture α to the X coordinate of the detector field 40 and the distance R of the scattering point P from the X-ray source O to the Y coordinate of the detector field 40. It allows only scattering radiations from a narrow angle range around the scattering angle Θ into the detector 4. This is achieved on the basis of its geometry, as represented in FIGS. 2 and 3.

FIG. 2 shows a cut section along the YZ plane through the secondary collimator 1. Vertical plates 11 can be recognized which run parallel to one another. These vertical plates 11 stand perpendicular to the YZ plane and are arranged inclined by the scattering angle Θ towards the Z axis. They are made of an absorbent material, for example steel, and are approximately 100 μm thick. Neighboring vertical plates 11 are spaced 1.5 mm apart from one another, which corresponds to the width of a detector element 40 in Y direction.

A section along the XZ plane is represented in FIG. 3. This plane contains the point at which the X-ray source O is arranged, as well as the starting point A and finishing point B of the detector 4. Horizontal plates 12 which are 1.5 mm high (perpendicular to the represented plane) (as described above in connection with FIG. 2) and 2 mm wide at the detector 4

(not represented) which corresponds to the width of an individual detector element 40, run perpendicular to the represented plane. The slits formed by the vertical plates 11 and the horizontal plates 12 narrow in the direction of the X-ray source O. The horizontal plates 12 are thus aligned such that they all point to the X-ray source O.

The slits are divided into a total of 5 modules 13 of the secondary collimator 1. Each module 13 is developed as a beam segment and has an aperture of 12° so that, in the case of a directly ensuing arrangement of the 5 modules 13, the resulting total aperture is the 60° of the aperture α of the fan beam 2. A module 13 extends for 27 mm in Y direction and 350 mm at the detector in X direction and 228 mm in X direction directly below the conveyor belt (not shown) on which the item of luggage 3 to be examined lies. Each module 13 is combined to form a collimator unit 10 and arranged in a vertical steel container so that, given a precise joining together of the modules 13, a precision of 30 μm results for the slits of the secondary collimator 1.

An as yet unfinished scattering collimator is represented in FIG. 4. The method of production of a module 13 of a secondary collimator 1 can be well described with the help of this figure.

A first metal sheet 15 is arranged on a robust and rigid base plate 14. The first metal sheet 15 is firmly connected to the base plate 14 by means of a known connection process, for example by gluing or spot welding. The metal sheet 15 was pre-shaped beforehand by means of a traditional metal-working method. The metal sheet 15 has been shaped such that vertical plates 11 and horizontal plates 12, in each case standing at 90° relative to each other, are formed in constant alternation. These are in each case connected to each other via a straight folding edge 16. It is clearly recognizable that the vertical plates 11 run in two planes parallel to each other, one constantly-rotating vertical plate 11 lying in the upper plane and then in the lower plane in constant alternation. Against this, the horizontal plates 12 do not run parallel to each other, but converge onto the X-ray source O (not shown).

During the connection step the pre-shaped metal sheet 15 is precisely fixed by means of a template which is formed from "forks" which are introduced into the slits 17.

In the next step an identically pre-shaped metal sheet 15 is arranged precisely above the most recently-attached metal sheet 15 and held precisely at this position by means of the above-described template during the connection, and firmly connected by means of one of the previously described connection processes to the metal sheet 15 attached there under. This method is repeated until all the metal sheets are precisely arranged one above the other. As a rule, 18 metal sheets 15 are arranged one above the other in order that the number of segments of the detector 4 in Y direction is achieved. A cover plate (not shown) is placed on the topmost metal sheet 15 and is connected by this metal sheet 15, like the base plate 14, to the first metal sheet 15. Thus a two-dimensional grid structure of the metal sheets 15 is achieved, through which the whole module 13 is actually stable under its own weight.

In addition to the described possibility of analyzing an item of luggage 3 over the whole width of the fan beam 2, it is equally possible to provide just one module 13 in the X-ray scattering device. Then merely an aperture of 12° is observed through the secondary collimator 1 and the detector field 40. Although this greatly reduces the costs of the X-ray scattering device, this is at the cost of a lower testing speed. In this case the device must be swiveled about the point which is defined by the X-ray source O, either in the direction of the aperture α or perpendicular to it, in order to simulate the missing sections of the primary fan beam 2.

In summary, it can be said that, through a secondary collimator 1 according to the invention, the angle of the scattering point P is projected onto the X coordinate of the detector field 40 and the distance R of scattering point P from the X-ray source O is projected onto the X coordinate of the detector field 40. The secondary collimator 1 allows only a small angle range around the scattering angle Θ to fall into the detector 4. A secondary collimator 1 according to the invention is simultaneously mechanically extremely stable, which leads to a high-precision XRs profile. Moreover, the secondary collimator 1 according to the invention is very easy to produce and of modular construction. Thus there can be an adjustment to the available financial resources through the choice of the number of modules 13 used, the number of modules 13 used being directly linked to the speed of testing of the item of luggage 3.

LIST OF REFERENCE NUMBERS

1 Secondary collimator
2 Fan beam
3 Item of luggage
4 Detector
10 Collimator unit
11 Vertical plate
12 Horizontal plate
13 Module
14 Base plate
15 Metal sheet
16 Folding edge
17 Slit
30 Movement direction
40 Detector element
41 First row of detectors
42 Second row of detectors
43 Transmission detector
A,B Starting, finishing point of the detector
D Transmission point
D' Scattering beam point
O X-ray source
P Scattering point
Q Axis
R Distance
α Aperture
Θ Scattering angle

What is claimed is:

1. A secondary collimator for an X-ray scattering device, comprising: horizontal plates and vertical plates arranged perpendicular thereto, the vertical plates being arranged parallel to one another and inclined by a pre-determinable scattering angle relative to a transmission direction of an X-ray beam, and the horizontal plates being aligned fan-shaped onto a single point, and the horizontal plates forming a rectangular grid with the vertical plates and being combined to form a collimator unit.

2. The secondary collimator according to claim 1, wherein the plates are made of an X-ray absorbing material and are less than 1 mm thick.

3. The secondary collimator according to claim 1 wherein at an end remote from the X-ray source, the rectangular grid is 1-10 mm wide in horizontal direction and 0.5-2.5 mm high in vertical direction per grid element.

4. The secondary collimator according to claim 1, wherein, at its end remote from the X-ray source, the collimator unit is 350 mm wide overall in direction of the vertical plates and at the same time, at its end near the X-ray source, is 228 mm wide overall in direction of the vertical plates and, towards X-ray source, is 250 mm high overall and has an aperture of 12°.

5. The secondary collimator according claim 1, wherein the collimator unit is arranged in a perpendicular steel container.

6. The secondary collimator according to claim 1, wherein five collimator units are joined together which have a total aperture of 60°.

7. The secondary collimator according to claim 1, wherein a number of metal sheets which have folded surfaces is arranged on a robust, rigid base plate, each of the adjoining surfaces standing perpendicular on one another and the first metal sheet being firmly connected to the base plate and the second metal sheet being firmly connected to the first metal sheet and the next metal sheet in each case being firmly connected to its predecessor.

8. The secondary collimator according to claim 7, wherein a total of 18 metal sheets are arranged on the base plate.

9. The secondary collimator according to claim 7, wherein, at the end opposite the base plate, the metal sheet being firmly connected to a robust, rigid cover plate.

10. The secondary collimator according to claim 1, wherein the single point includes an X-ray source.

11. The secondary collimator of claim 1 wherein the plates are approximately 100 μm thick.

12. The secondary collimator of claim 1 wherein the plates are made of steel.

13. An X-ray scattering device for baggage check with an X-ray source, comprising: a primary collimator which only lets through a fan beam, the secondary collimator of claim 1 for imaging an area of an item of luggage and a scattering detector, the secondary collimator being arranged between the item of luggage to be examined and the scattering detector.

14. The X-ray scattering device according to claim 13, wherein a transmission detector is arranged additionally in straight extension from the X-ray source over the area to be examined of the item of luggage.

15. The X-ray scattering device according to claim 13, wherein the secondary collimator is aligned in vertical direction parallel to the fan beam and is aligned in horizontal direction to the area to be examined of the item of luggage.

* * * * *